United States Patent [19]

Oka et al.

[11] Patent Number: 5,747,306
[45] Date of Patent: May 5, 1998

[54] PROCESS FOR PRODUCING 2-KETO-L-GULONIC ACID USING ELECTRODIALYSIS

[75] Inventors: Masahide Oka, Kawanishi; Kenkichi Yoneto; Takamasa Yamaguchi, both of Kobe, all of Japan

[73] Assignee: Takeda Chemical Industries, Ltd., Osaka, Japan

[21] Appl. No.: 517,660

[22] Filed: Aug. 22, 1995

Related U.S. Application Data

[63] Continuation of Ser. No. 271,940, Jul. 8, 1994, abandoned.

[30] Foreign Application Priority Data

Jul. 9, 1993 [JP] Japan ..................................... 5-170247

[51] Int. Cl.$^6$ ........................................................ C12P 7/60
[52] U.S. Cl. ............................. 435/138; 435/42; 426/239
[58] Field of Search ..................... 435/138, 17, 42; 204/182.3, 182.4, 182.5, 186.4; 426/239

[56] References Cited

U.S. PATENT DOCUMENTS

| | | | |
|---|---|---|---|
| 3,873,425 | 3/1975 | Kobayashi et al. | 195/36 R |
| 4,877,735 | 10/1989 | Nogami et al. | 435/138 |
| 4,882,277 | 11/1989 | Czytko et al. | 435/136 |

FOREIGN PATENT DOCUMENTS 0 221 707    5/1987    European Pat. Off. .

63-148979    6/1988    Japan .

OTHER PUBLICATIONS

Oka, S. et al., *Chemical Abstracts* vol. 110, No. 171826t 1989.

Von Eysmondt, J. et al., *Chemical Abstracts* vol. 112, No. 160996p 1990.

Von Eysmondt J. et al. *Chemical Abstracts*, vol. 113, No. 113717j, 1990.

Nomura, Y et al, "Acetic Acid Production by an Electrodialysis Fermentation Method with a Computerized Control System", *Applied and Environmental Microbiology*, vol. 54 No. 1 pp. 137–142 1988.

Weir, A.J. et al., "Recovery of Propionic and Acetic Acids from Fermentation Broth by Electrodialysis", *Biotechnol Prog.* vol. 8, pp. 479–485, 1992.

Perry's Chemical Engineer's Handbook, pp. 17-34→17-45, 1984.

*Primary Examiner*—Irene Marx
*Attorney, Agent, or Firm*—Wenderoth, Lind & Ponack

[57] ABSTRACT

In a microbial process for producing 2-keto-L-gulonic acid (hereinafter sometimes referred to as 2KGA) by fermentation or microbial cell reaction with at least one microorganism capable of producing 2KGA, wherein the improvement comprises taking out, from the fermentation broth or microbial cell reaction mixture, the produced 2KGA alone or together with a low molecular-weight cation as the counter ion by electrodialysis.

2 Claims, 2 Drawing Sheets

PROCESS FOR PRODUCING 2-KETO-L-GULONIC ACID USING ELECTRODIALYSIS

This application is a continuation of now abandoned application Ser. No. 08/271,940, filed Jul. 8, 1994.

FIELD OF THE INVENTION

The present invention relates to a process for producing 2-keto-L-gulonic acid (hereinafter sometimes referred to as 2KGA) useful as an intermediate for L-ascorbic acid production using microorganisms. Specifically, it relates to so-called electrodialysis fermentation wherein, in fermentation or microbial cell reaction producing 2KGA as an end product, 2KGA alone or 2KGA together with a low-molecular weight counter cation is taken out or separated by electrodialysis from the culture broth or microbial cell reaction mixture.

Hereinafter, "fermentation or microbial cell reaction producing 2KGA as an end product" is sometimes referred to as "2KGA fermentation" briefly. The "fermentation" sometimes includes the "microbial cell reaction". The "culture broth" sometimes includes the "microbial cell reaction mixture".

BACKGROUND OF THE INVENTION

2-Keto-L-gulonic acid which is useful as an intermediate for synthesizing L-ascorbic acid has been produced by the industrially established so-called Reichschtein method (see Helvetica Chemica Acta, Vol. 17, p.311 (1934)). However, this method involves many steps and requires a large amount of organic solvents, and therefore is insufficient for industrial technology of today.

On the other hand, as alternatives of the Reichschtein method, several methods mainly employing microorganisms have been proposed. They include, for example, a method which comprises subjecting D-glucose to microbial oxidation to give 2,5-diketo-D-gluconic acid which is then subjected to microbial or chemical reduction to give 2KGA (see JP-B 39-14493, JP-B 53-25033, JP-B 56-15877, JP-B 59-3592), a method which comprises introducing the 2,5-diketo-D-gluconic acid reductase gene of Corynebacterium into Erwinia which is capable of producing 2,5-diketo-D-gluconic acid according to DNA recombination technique to obtain 2KGA from D-glucose by a one-step fermentation process (Science, Vol. 230, p. 144 (1985)), and a method which comprises oxidizing the starting material D-sorbitol or L-sorbose with a microorganism belonging to the genus Gluconobacter to give 2KGA (see JP-A 2-150287).

The bacterial strain Pseudogluconobacter saccharoketogenes capable of efficiently converting L-sorbose to 2KGA was isolated from soil (see EP-B-0221707 (JP-A 62-228288)). USP 4877735 (JP-A 64-85088) discloses an efficient process for producing 2KGA from L-sorbose using the above microorganism based on the finding that addition of a rare earth element to the medium significantly promotes the 2KGA production by this microorganism.

These prior art methods use the cultivation method called batch culture or fed-batch culture which comprises adding a substrate such as a sugar, sugar alcohol, sugar acid, etc., at the beginning of the cultivation in one portion or adding a part or all of it semicontinuously or continuously during cultivation, and stopping the cultivation when the resulting 2KGA is accumulated in a sufficient amount and further cultivation does not efficiently convert the substrate to 2KGA.

However, these methods are not necessarily satisfactory in terms of the time required for the converting reaction and the concentration of the product in the final reaction mixture. There are various probable reasons for such a result such as the inhibition of the production by the resulting product, alkaline salts added as neutralizing agents, or complex effects of them.

On the other hand, in organic acid fermentation such as lactic acid fermentation, acetic acid fermentation, etc., the so-called electrodialysis fermentation has been tried to prevent the inhibition by the resulting product, alkaline salts added as neutralizing agents or complex effects of them (see U.S. Pat. No. 3,873,425 (JP-B 56-50958), U.S. Pat. No. 4,882,277 (JP-A 62-146595), Abstract of the annual meeting of Nippon Hakko Kogakukai (Japan Fermentation Technology Association (1991)). In the electrodialysis fermentation, by electrifying the culture broth in an electrodialysis apparatus having cation-exchange membranes and anion-exchange membranes, if necessary, bipolar membranes between the anode and cathode, the resulting organic acid alone or together with a low molecular-weight cation as the counter ion is separated from the culture broth to maintain the concentration thereof in the culture broth substantially at a low level.

JP-A 63-148979 discloses electrodialysis fermentation wherein, in the electrodialysis apparatus, the product obtained by the fermentation is separated from the fermentation broth by electrodialysis in the presence of polyphosphoric acid or its salt.

However, these techniques have not been applied to the fermentation giving 2KGA as the end product.

OBJECTS OF THE INVENTION

The main object of the present invention is to provide an efficient process for producing 2-keto-L-gulonic acid useful as an intermediate for L-ascorbic acid production using microorganisms.

This object as well as other objects and advantages of the present invention will become apparent to those skilled in the art from the following description with reference to the accompanying drawings.

SUMMARY OF THE INVENTION

The present inventors have intensively studied to find an advantageous cultivating method in 2KGA fermentation and tried to apply electrodialysis fermentation to 2KGA fermentation. As a result, it has been found that separation of 2KGA from the culture broth by electrodialysis in this fermentation can remarkably shorten the culture time compared with conventional batch culture or fed-batch culture when the same amount of substrates are oxidized, and it has also been found that the prolonged culture time and additional feeding of the substrate can remarkably increase the amount of 2KGA obtainable in one culture. Thus, the present invention has been completed.

That is, the present invention provides an improved microbial process for producing 2KGA by fermentation or microbial cell reaction with at least one microorganism capable of producing 2KGA, wherein the improvement comprises taking out, from the fermentation broth or microbial cell reaction mixture, the produced 2KGA alone or together with a low molecular-weight cation as the counter ion by electrodialysis.

DETAILED DESCRIPTION OF THE INVENTION

Figure 1:
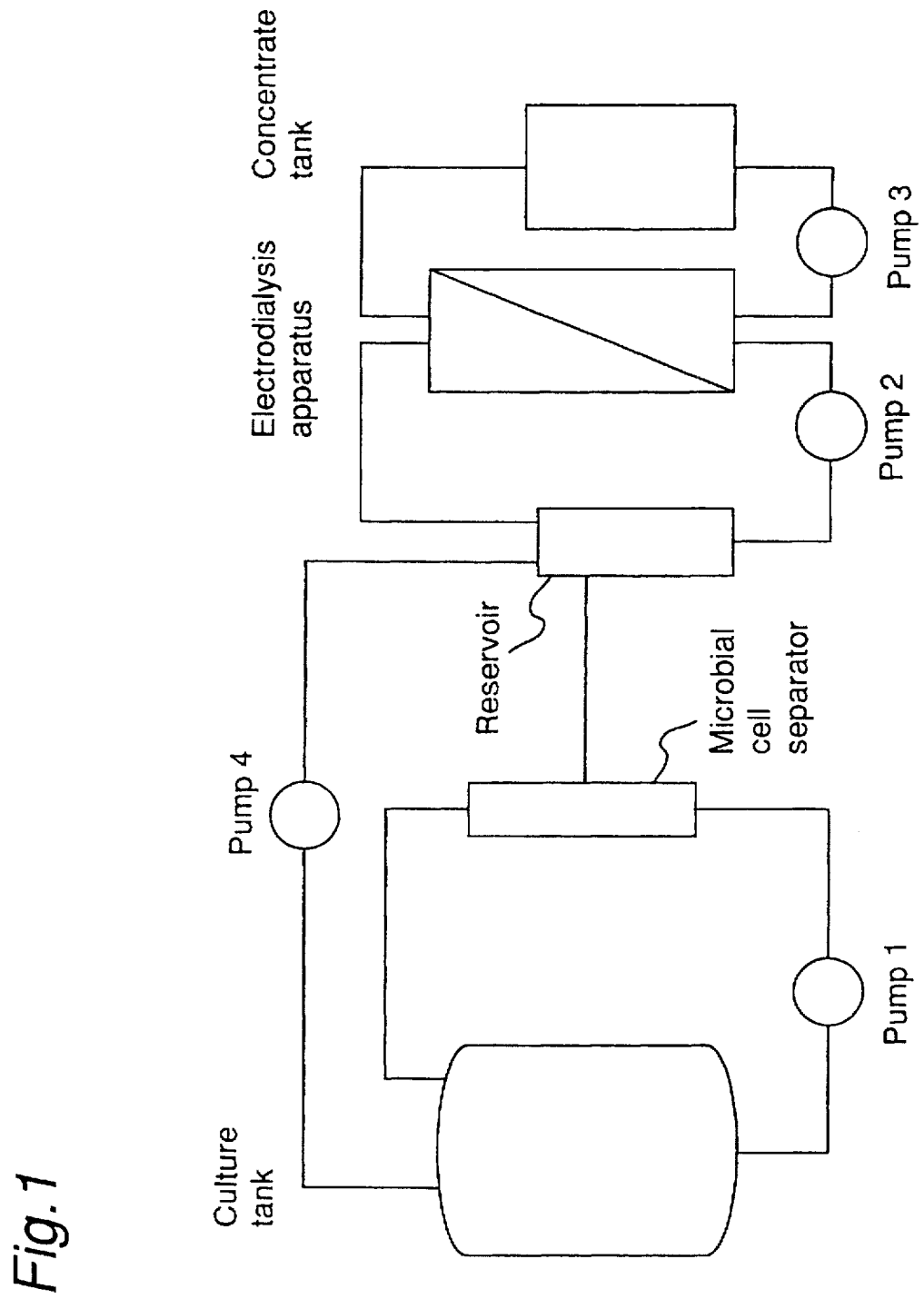
FIG. 1 is a diagram of an exemplary apparatus used for the present invention.

Examples of the microorganisms capable of producing 2KGA to be used in the present invention include known bacteria belonging to the genera Pseudogluconobacter, Gluconobacter, Pseudomonas and Corynebacterium, and bacteria belonging to the genus Erwinia having introduced 2,5-diketo-D-gluconic acid reductase gene. Of course, the microorganisms to be used in the present invention are not limited to these microorganisms, and any microorganisms can be used as long as they are capable of producing 2KGA. In particular, bacteria belonging to the genus Pseudogluconobacter can preferably be used. Examples of the bacteria belonging to the genus Pseudogluconobacter include *Pseudogluconobacter saccharoketogenes* K591s (FERM BP-1130), 12-5 (FERM BP-1129), TH14-86 (FERM BP-1128), 12-15 (FERM BP-1132), 12-4 (FERM BP-1131), 22-3 (FERM BP-1133), etc., described in EP-B-0221707.

The cultivation conditions such as medium formulation, cultivation temperature, etc., may be so controlled as to be suitable for the strains to be used. For example, in 2KGA fermentation using bacteria belonging to the genus Pseudogluconobacter, it has been found that the fermentation can be promoted by mixed culture with bacteria belonging to the genera Bacillus, etc. (EP-B-0221707 (JP-A 62-228288)). The mixed culture can be applied to the present invention.

For example, in working the present invention into practice by incubating the Pseudogluconobacter strain (hereinafter sometimes referred to as the oxidative bacteria or strain) in an L-sorbose-containing liquid medium to produce 2-keto-L-gulonic acid in the broth, it has been found that the production yield of 2-keto-L-gulonic acid is remarkably higher when other bacteria (hereinafter sometimes referred to as the concomitant bacteria or strain) are allowed to be present in combination with the Pseudogluconobacter oxidative strain than it is the case when the oxidative strain alone is cultivated.

The bacteria that are allowed to be present concomitantly may for example be bacteria of the following genera: Bacillus, Pseudomonas, Proteus, Citrobacter, Enterobacter, Erwinia, Xanthomonas and Flavobacterium. As the specific species, the following may be mentioned.

*Bacillus cereus* IFO 3131
*Bacillus licheniformis* IFO 12201
*Bacillus megaterium* IFO 12108
*Bacillus pumilus* IFO 12090
*Bacillus amyloliquefaciens* IFO 3022
*Bacillus subtilis* IFO 13719
*Bacillus circulans* IFO 3967
*Pseudomonas trifolii* IFO 12056
*Pseudomonas maltophilia* IFO 12692
*Proteus inconstans* IFO 12930
*Citrobacter freundii* IFO 13544
*Enterobacter cloacae* IFO 3320
*Erwinia herbicola* IFO 12686
*Xanthomonas pisi* IFO 13556
*Xanthomonas citri* IFO 3835
*Flavobacterium menigosepticum* IFO 12535
*Micrococcus varians* IFO 3765
*Escherichia coli* IFO 3366

Any of these strains may be incubated in an appropriate medium at 20° to 40° C. for 1 to 4 days and the resulting culture is used as an inoculum for cultivation in the presence of said concomitant bacteria. The inoculum size is generally desirably $1/10$ to $1/1000$ of that of the oxidative strain. When the concomitant strain in this amount is incubated with the oxidative strain, the growth of the oxidative strain is promoted so that compared with a pure culture of the oxidative strain, the mixed culture is able to oxidize L-sorbose to 2-keto-L-gulonic acid in higher concentration in a shorter time period. The bacteria used as said concomitant bacteria are preferably those which cannot assimilate or only sparingly assimilate L-sorbose and 2-keto-L-gulonic acid. Otherwise, the same cultivation conditions as those of the pure culture of the oxidative strain can be employed. The medium used for cultivation of the above-mentioned microorganisms may be a liquid or solid medium containing nutrients which can be utilized by the said strain. However, for mass production, a liquid medium is preferred. The medium contains the carbon sources, nitrogen sources, inorganic salts, organic acid salts and trace nutrients which are generally used in the cultivation of microorganisms. While the starting material L-sorbose serves as the carbon source, other auxiliary carbon sources such as glucose, glycerin, sucrose, lactose, maltose, molasses, etc., can also be employed. The nitrogen sources are exemplified by various inorganic and organic nitrogen-containing compounds or nitrogenous materials such as ammonium salts (e.g., ammonium sulfate, ammonium nitrate, ammonium chloride, ammonium phosphate, etc.), corn steep liquor (CSL), peptone, meat extract, yeast extract, dried yeast, soybean flour, cottonseed meal, urea, and so on. As the inorganic salts, there may be employed salts of potassium, sodium, calcium, magnesium, iron, manganese, cobalt, zinc, copper and/or phosphoric acid.

As the trace nutrients, in addition to CoA, pantothenic acid, biotin, thiamine and riboflavine which are essential growth factors for said microorganisms, there can be added such substances so as to promote the growth of the microorganisms and the production of 2-keto-L-gulonic acid thereby, such as flavine mononucleotide (FMN), flavine adenine dinucleotide (FAD), other vitamins, L-cysteine, L-glutamic acid, sodium thiosulfate, etc., either in the form of pure chemical compounds or in the form of natural materials containing them, in suitable amounts.

With regard to the cultural method, any stationary culture, shaking culture, submerged culture, and so on can be employed. For mass production, the so-called submerged culture is preferred.

Of course, the cultural conditions depend on the bacterial strain, medium composition, and other factors, and can be chosen in each case so that the object compound may be obtained with the highest efficiency. Thus, for example, the incubation temperature may advantageously be in the range of 25° to 35° C. and the medium pH may be about 5 to 9.

As the pH value of the medium generally lowers with the formation of the object compound, it may be advantageous to add a suitable basic substance such as sodium hydroxide, potassium hydroxide or ammonia from time to time so as to maintain the medium at an optimal pH level for the elaboration of 2-keto-L-gulonic acid by the bacterial strain or have a suitable buffer agent contained in the medium to thereby keep the medium pH constant.

Aside from the above, the sterilized culture broths of bacteria other than the oxidative strains can be used advantageously as medium components. The bacteria that can be utilized in this manner include those of the genus Bacillus, the genus Pseudomonas, the genus Citrobacter, the genus Escherichia, and the genus Erwinia, for instance. Specifically, the following bacteria may be mentioned.

| | |
|---|---|
| *Bacillus cereus* | IFO 3131 |
| *Bacillus subtilis* | IFO 3023 |
| *Bacillus pumilus* | IFO 12089 |
| *Bacillus megaterium* | IFO 12108 |
| *Bacillus amyloliquefaciens* | IFO 3022 |
| *Pseudomonas trifolii* | IFO 12056 |
| *Citrobacter freundii* | IFO 12681 |
| *Escherichia coli* | IFO 3546 |
| *Erwinia herbicola* | IFO 12686 |

Thus, these bacteria are incubated in media which permit their growth at 20° to 40° C. for 2 to 4 days and the resulting culture broths are sterilized and added to the medium for the oxidative strain in a proportion of 0.5 to 5.0 percent (V/V). In this manner, growth of the oxidative strain can be encouraged.

In the present invention, there can also be used conventional fermentation methods wherein a main fermentation medium is inoculated with a small amount of a seed culture broth and 2KGA is produced with the growth of the microorganisms. Alternatively, microorganisms capable of producing 2KGA prepared in advance can be used for the microbial cell reaction method that is not substantially accompanied by the growth of the microorganisms. Combination methods thereof can also be used.

In the above-mentioned conventional fermentation methods, electrodialysis is preferably started when the microorganisms have sufficiently been grown. In the microbial cell reaction method and, in some cases, in the fermentation methods, however, electrodialysis can be carried out from the beginning of the reaction to substantially shorten the cultivation time.

In the present invention, the culture broth in the fermentor or reaction tank is introduced into an electrodialysis apparatus equipped with ion-exchange membranes and if necessary, bipolar membranes, if necessary, after removing the bacterial cells by filtration, centrifugation, etc., and electrified for electrodialysis to take out or separate 2KGA from the culture broth alone or together with a low-molecular weight cation as the counter ion such as univalent or bivalent low molecular-weight cations (e.g., $Li^+$, $Na^+$, $K^+$, $Ca^{2+}$, $Mg^{2+}$, $NH_4^+$, etc.). Then, 2KGA is recovered by conventional methods.

Figure 2:
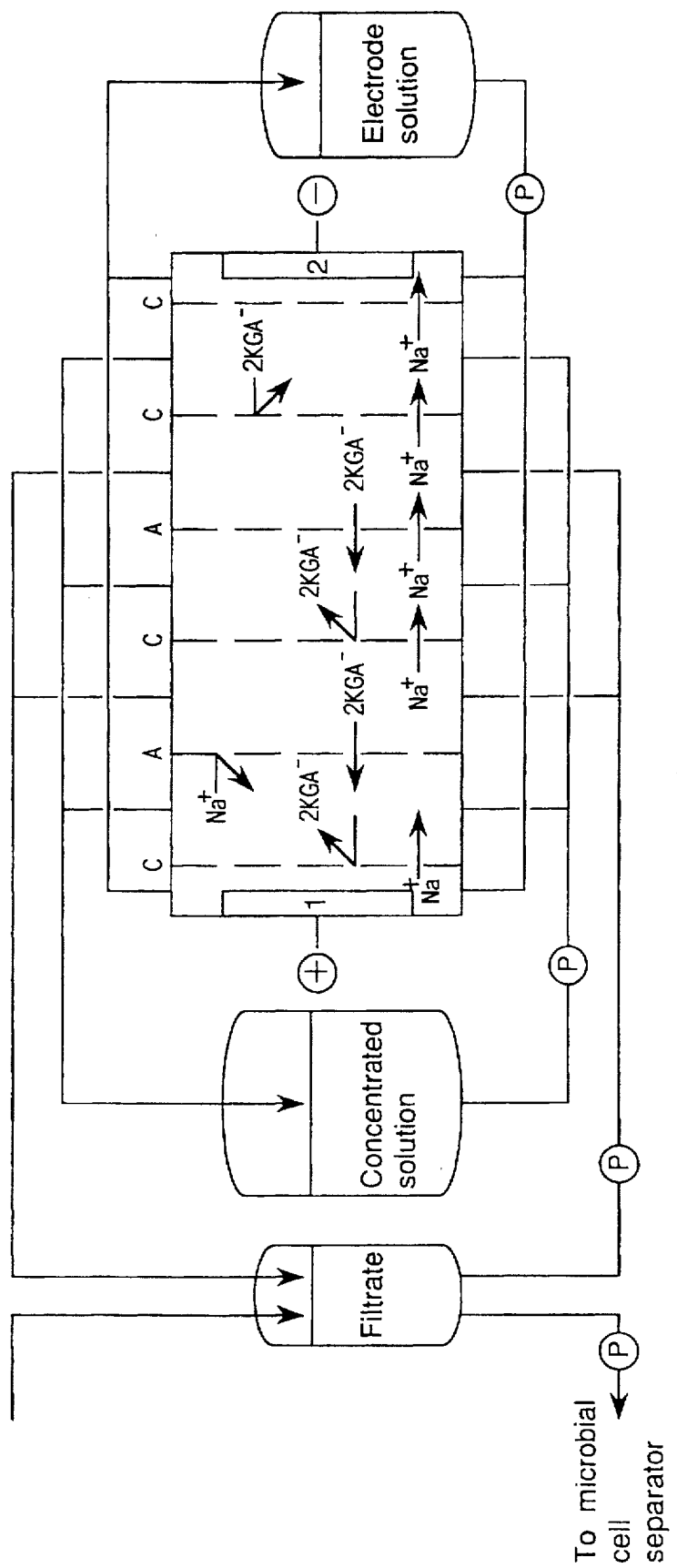
FIG. 2 is a diagram of an exemplary electrodialysis apparatus. In this figure, A is an anion-exchange membrane through which anions pass and cations do not. C is a cation-exchange membrane through which cations pass and anions do not. P is a pump.

An example of the electrodialysis apparatus used in the present invention is the apparatus in FIG. 2 equipped with the cation-exchange membrane C and anion-exchange membrane A by turns between the anode 1 and cathode 2. Normally, one or more pairs of ion-exchange membranes are preferably used. As the ion-exchange membranes in the electrodialysis in the present invention, known ion-exchange membranes (anion-exchange and cation-exchange membranes), particularly commercially available ones can be used. In particular, commercially available ones such as Neosepta® (manufactured by Tokuyama Co., Ltd.), Selemion® (manufactured by Asahi Glass Company Co., Ltd.), etc., can be used.

The anion-exchange membranes have pores that permit the efficient passage of the desired product 2KGA. Further, they are preferably those having as small substrate leakage as possible and as low electric resistance as possible.

As the electrode solution, acids or alkalis such as $H_2SO_4$, $HNO_3$, NaOH, KOH, etc., or solutions of alkaline metal salts such as $Na_2SO_4$, $K_2SO_4$, $NaNO_3$, $KNO_3$, etc., can be used. For the electrodialysis using the apparatus as shown in FIG. 2, a solution of alkaline metal salts is normally used. When $Ca^{2+}$, $Ba^{2+}$, etc., are present in the fermentation broth or filtrate thereof, a solution of $NaNO_3$ or $KNO_3$ is preferably used.

The electrodialysis apparatus to be used may have the structure wherein 2KGA is separated in the free form from the culture broth or reaction mixture and low molecular-weight cations as the counter ions can be put back into the culture tank or reaction tank to reduce the amount of alkalis such as sodium hydroxide, ammonia, etc., to prevent the pH decrease during the cultivation. Industrially, electrodialysis apparatus with the structures to take out 2KGA together with the added alkaline cations are preferred because they are compact and have simple structures and good dialysis efficiency. For example, commercially available electrodialysis apparatus such as Micro Acilyzer (manufactured by Asahi Chemical Industry Co., Ltd., Japan), etc., can be used.

When the electrodialysis is carried out, the culture broth or fermentation reaction mixture may directly be introduced into the electrodialysis apparatus. Preferably, to prevent deterioration of properties of the electrodialysis membranes, however, a step for separating microbial cells such as filtration, centrifugation, etc., is preferably added to the process, and the microbial cells are recycled to the culture tank, while the clarified solution is subjected to electrodialysis. For the filtration, cross flow type filters such as hollow fiber membrane filters or ceramic membrane filters are normally used. These filters are preferably used at a high circulation flow rate to increase the filtration efficiency. To increase the filtration efficiency at a low circulation flow, vortex flow filters such as commercially available Benchmark or Pacesetter (Membrex, Inc., U.S.A.) are preferably used. The attached FIG. 1 is a diagram of an example of the apparatus used in this process.

In working the present invention into practice by using this apparatus, the culture broth from the culture tank is passed by the pump 1 through the microbial cell separator, normally filtration apparatus, to filter the broth. The microbial cells are recycled to the culture tank. The filtrate is kept in the reservoir, then introduced into the electrodialysis apparatus via pump 2 and subjected to electrodialysis. The concentrated solution dialyzed in the electrodialysis apparatus is introduced into the concentrated solution tank (concentrate tank) via pump 3 and sent to the later recovering step. The filtrate that has passed through the electrodialysis apparatus is put back into the reservoir. The filtrate and recovered solution from the electrodialysis apparatus in the reservoir can be recycled to the culture tank via pump 4.

When the electrodialysis is used, the concentration of 2KGA in the culture broth is intermittently or continuously controlled to the region that does not remarkably inhibit the 2KGA production of the strains to be used. For example, when bacteria belonging to the genus Pseudogluconobacter are used, the electrodialysis is carried out while maintaining the 2KGA concentration at not more than 80 mg/ml, preferably not more than 50 mg/ml. The substrate may be added in one portion, but it is advantageous to continuously add it so as to continuously maintain the concentration of the remaining substrate in the culture broth at a low level.

For example, when bacteria belonging to the genus Pseudogluconobacter are used, considering the 2KGA production efficiency, the substrate concentration is maintained at 5 to 50 mg/ml, preferably 10 to 30 mg/ml. As described above, the substrate may be added in one portion, but it is preferred that a part or all of it is added continuously or in several divided portions. Further, during the cultivation, there can be added substances that keep or promote the 2KGA production, for example, organic nutrients such as yeast extract, corn steep liquor, etc.; trace nutrients such as vitamins, amino acids and nucleic acids; inorganic acids, etc.

As the substrate, sugars, sugar alcohols, sugar acids, etc., can be used. In particular, it is efficient to treat L-sorbose, D-sorbitol, L-sorboson, etc., with the above microorganisms.

The culture medium and conditions including the cultivating method can appropriately be selected depending on the microorganisms and substrate to be used. For example, in the case of cultivation using bacteria belonging to the genus Pseudogluconobacter, the media and culture conditions described in the above EP-B-0221707 (JP-A 62-228288) can be used. In the case of the culture using bacteria belonging to the genus Pseudomonas, the conditions described in JP-A 63-112989 or a modification thereof can be used.

When the substrate added to the culture broth is sufficiently converted to 2KGA, the electrodialysis is stopped. The resulting 2KGA may be recovered from both of the culture broth and concentrated solution. It is advantageous for 2KGA purification to continue the electrodialysis to move all of 2KGA in the culture broth to the concentrated solution and recover 2KGA from the solution. 2KGA can be recovered from the culture broth or concentrated solution by conventional methods such as column chromatography using ion-exchange resin columns, concentration, or crystallization or recrystallization by adding solvents.

As described hereinabove, the present invention can remarkably shorten the culture time compared with conventional fermentation or microbial cell reaction methods when the same amount of substrates are oxidized, and the present invention can remarkably increase the amount of 2KGA obtainable in one culture.

The following examples illustrate the present invention in detail but are not to be construed to limit the scope thereof.

The determination of 2KGA was carried out by high performance liquid chromatography (HPLC) under the following conditions.

The conditions for the HPLC.

Column: SCR101H, 300×7 mm (manufactured by Shimadzu Corp., Japan), column temperature: 30° C.

Mobile phase: 4mM sulfuric acid.

Detector: RI detector.

EXAMPLE 1

1) Comparative experiment (standard culture)

The seed culture medium A (20 ml) having the formulation in Table 2 was placed in a 200 ml Erlenmeyer flask and sterilized at 120° C. for 20 minutes. The flask was inoculated with one loopful of *Pseudogluconobacter saccharoketogenes* K591s (IFO 14464, FERM BP-1130, hereinafter sometimes referred to as the oxidative bacteria) grown on a slant medium in Table 1 at 30° C. for 3 days, and incubated at 28° C. with shaking for a day to give the first seed culture broth. Likewise, the seed culture medium A (200 ml per flask) was placed in two 1 liter Erlenmeyer flasks and sterilized, and each of the flasks was inoculated with the first seed culture broth (10 ml) and incubated with shaking at 28° C. for 2 days to give the second seed culture broth. The seed culture medium B (20 ml) having the formulation in Table 3 was placed in a 200 ml Erlenmeyer flask and sterilized. The flask was inoculated with one loopful of *Bacillus megaterium* IFO 12108 and incubated with shaking at 28° C. for 2 days to give a seed culture broth of *Bacillus megaterium* (hereinafter referred to as the concomitant bacteria).

Tap water was added to a mixture of L-sorbose (50 g), corn steep liquor (CSL)(60 g), $FeSO_4$ (3 g), ammonium sulfate (9 g), vitamin $B_2$ (3 mg) and sucrose (1.5 g) to a final volume of 1660 ml. The resulting mixture was adjusted to pH 7 with NaOH and sterilized to give a main fermentation medium. To this was added the second seed culture broth (300 ml) of the oxidative bacteria, the seed culture broth (4 ml) of the concomitant bacteria and a sterilized solution of crude rare earth chloride (Mitsubishi Chemical Industries, Ltd., Japan)(0.3 g) in water (10 ml). The mixture was placed in a sterilized 5 liter jar fermentor. The incubation was started at 32° C. at an agitating rate of 800 rpm and at an aeration rate of 0.5 vvm. The pH of the mixture was maintained at 6.2 by automatically adding 30% NaOH using a peristaltic pump interlocked with a pH sensor. A sterilized solution (900 ml) of L-sorbose (400 g) in tap water was continuously added to the above culture so that the concentration of the L-sorbose in the culture broth became about 10 to 30 mg/ml. As a result, all of the L-sorbose (total amount: 450 g) was oxidized 40 hours after the beginning of the cultivation, and 2KGA (354 g in terms of the free form; hereinafter 2KGA weight is indicated in terms of the free form) was accumulated in the culture broth.

2) Culture with electrodialysis

As shown in FIG. 1, another sterilized 5 liter jar fermentor as a culture tank was connected to the microbial cell separator having hollow fiber membranes (Microza PMP102, manufactured by Asahi Chemical Industry Co., Ltd., Japan) and to an electrodialysis apparatus (Micro Acilyzer G3, manufactured by Asahi Chemical Industry Co., Ltd., Japan), and provided with dialysis membranes (AC-120-800, manufactured by Asahi Chemical Industry Co., Ltd., Japan). The same main fermentation medium, oxidative bacteria seed culture broth, concomitant bacteria seed culture broth and a sterilized aqueous solution of crude rare earth chloride as those described above were added to the jar fermentor which is sterilized previously, and cultivation was started under the same conditions as those described above. A sterilized solution (900 ml) of L-sorbose (400 g) in tap water was continuously added in the same manner while controlling the pH by the above method. Until 9 hours after the beginning of the cultivation, normal cultivation was carried out with the pump stopped. From 9 hours, the culture broth was circulated between the hollow fiber membrane filter and the jar fermentor using the pump at a flow rate of 3 liters/min. The effluent filtrate was circulated to the electrodialysis apparatus through the reservoir (0.5 liter volume) at a flow rate of 1 liter/min. The filtrate exceeding 0.5 liters was flowed back to the jar fermentor. All apparatus and connecting tubes used except the jar fermentor were sterilized with 0.5% sodium hydroxide and 0.5% sodium hypochlorite, and rinsed with sterilized water previously. Electrodialysis was started, and the electrodialysis apparatus was operated so that the 2KGA concentration does not exceed 50 mg/ml. As a result, a total of 450 g L-sorbose was completely oxidized 22 hours after the beginning of the cultivation. Substantially all of the 2KGA formed in the culture broth was recovered to the concentrated solution (final volume: 1.8 liters) by the electrodialysis for additional 2 hours, and 360 g of 2KGA was obtained.

TABLE 1

| Slant medium (g/l) | |
| --- | --- |
| D-sorbitol | 25 |
| Peptone | 10 |
| Yeast extract | 10 |
| $CaCO_3$ | 2 |
| Agar | 20 |

TABLE 2

| Seed medium A (g/l) | |
| --- | --- |
| Lactose | 10 |
| Yeast extract | 10 |
| CSL | 30 |
| Ammonium sulfate | 3 |
| pH | 7.0 |

TABLE 3

| Seed medium B (g/l) | |
| --- | --- |
| Sucrose | 40 |
| Proflo | 40 |
| $K_2HPO_4$ | 6.5 |
| $KH_2PO_4$ | 5.5 |
| NaCl | 0.5 |
| Ammonium sulfate | 0.5 |
| $MgSO_4 \cdot 7H_2O$ | 0.05 |
| Calcium pantothenate | 0.25 |
| pH | 7.0 |

EXAMPLE 2

According to the same manner as that described in Example 1, standard cultivation was carried out. All of the sorbose was oxidized by the 40-hour cultivation, and 356 g of 2KGA was accumulated in the culture broth.

Electrodialysis fermentation was carried out according to the same manner as in Example 1 except feeding conditions of L-sorbose. The feeding was carried out by continuously adding a sterilized solution (2700 ml) of L-sorbose (1150 g) in tap water in the same manner as in Example 1.

As a result, all of the L-sorbose was oxidized by the 36-hour cultivation. At this point, aeration and agitation of the jar fermentor was stopped. By continuing the electrodialysis for 2 hours, substantially all of the 2KGA in the culture broth and the filtrate from the hollow fiber membrane filter was recovered to the concentrated solution, and 960 g of 2KGA was obtained in the concentrated solution (final volume: 4.5 liters).

EXAMPLE 3

1) Pure culture with electrodialysis

A jar fermentor with electrodialysis apparatus was prepared according to the same manner as in Example 1, 2) except that a vortex flow filter (Benchmark System; Membrex, Inc., U.S.A.) equipped with Ultraphilic MX-100 Ultra Filter (Membrex, Inc., U.S.A.) was used instead of the hollow fiber membrane filter (Microza PMP 102) of the microbial cell separator in FIG. 1.

Tap water was added to a mixture of L-sorbose (50 g), corn steep liquor (CSL)(60 g), $FeSO_4$ (3 g), ammonium sulfate (9 g), vitamin $B_2$ (3 mg), sucrose (1.5 g) and yeast extract (30 g) to a final volume of 1660 ml. The resulting mixture was adjusted to pH 7 with NaOH and sterilized to give a main fermentation medium. To this was added the seed culture broth of the oxidative bacteria and an aqueous solution of crude rare earth chloride. Then the cultivation was started. A 50 w/v % aqueous solution of L-sorbose was used for feeding. As in Example 1, the pH during the cultivation was maintained at 6.2 by using 30% NaOH.

From 9 hours after the beginning of the cultivation, the microbial cells were filtered by circulating the culture broth between the jar fermentor and the vortex flow filter at a flow rate of 0.25 liters/min using the pump. The resulting filtrate was subjected to electrodialysis according to the same manner as in Example 1. Table 4 shows the profile of the oxidation rate of L-sorbose per jar fermentor. The cultivation, the filtration of microbial cells and the electrodialysis were stopped after 60 hours at which the oxidation rate became inefficient value. As a result, 1923 g of L-sorbose was oxidized, and 1300 g of 2KGA was obtained in the concentrated solution and a total amount of 187 g of 2KGA was obtained in the culture broth and filtrate. Thus, a total amount of 1487 g of 2KGA was obtained.

TABLE 4

| Culture time (Hr) | Oxidation rate of sorbose (g/Hr) |
| --- | --- |
| 0 | 0.0 |
| 5 | 6.0 |
| 10 | 33.2 |
| 15 | 42.3 |
| 20 | 40.2 |
| 25 | 41.3 |
| 30 | 43.2 |
| 35 | 42.0 |
| 40 | 40.2 |
| 45 | 40.3 |
| 50 | 38.2 |
| 55 | 24.0 |
| 60 | 10.2 |

2) Mixed culture with electrodialysis

In an apparatus for electrodialysis culture equipped with a vortex flow filter, cultivation was conducted according to the same manner as in Example 3, 1) except that the main fermentation medium containing no yeast extract was used and at the beginning of the cultivation, the seed culture broth (4 ml) of the concomitant bacteria prepared according to the same manner as in Example 1 was added.

As described above, electrodialysis cultivation was started 9 hours after the beginning of the cultivation. Table 5 shows the profile of the oxidation rate. The cultivation, the filtration of microbial cells and the electrodialysis were stopped after 150 hours. As a result, 5720 g of L-sorbose was oxidized, and 4277 g of 2KGA was obtained in the concentrated solution and a total amount of 200 g of 2KGA was obtained in the culture broth and filtrate. Thus, a total amount of 4477 g of 2KGA was obtained.

TABLE 5

| Culture time (Hr) | Oxidation rate of sorbose (g/Hr) |
| --- | --- |
| 0 | 0.0 |
| 5 | 6.7 |
| 10 | 37.2 |
| 20 | 39.2 |
| 30 | 42.1 |
| 40 | 41.3 |

TABLE 5-continued

| Culture time (Hr) | Oxidation rate of sorbose (g/Hr) |
|---|---|
| 50 | 40.2 |
| 60 | 41.1 |
| 70 | 42.2 |
| 80 | 41.2 |
| 90 | 41.3 |
| 100 | 40.7 |
| 110 | 41.5 |
| 120 | 42.2 |
| 130 | 41.1 |
| 140 | 40.8 |
| 150 | 40.9 |

As is clear from the above results, in the pure culture 1), a high oxidation rate of L-sorbose was maintained only for 50 hours after the beginning of the cultivation, whereas, in the mixed culture 2), a high oxidation rate was maintained even after 150 hours from the beginning of the cultivation.

What is claimed is:

1. In a microbial process for producing 2-keto-L-gulonic acid (2KGA) by fermentation or microbial cell reaction with a microorganism capable of producing 2KGA selected from the group consisting of *Pseudogluconobacter saccharoketogenes* K591s (FERM BP-1130), *Pseudogluconobacter saccharoketogenes* TH14-86 (FERM BP-1128), *Pseudogluconobacter saccharoketogenes* 12-5 (FERM BP-1129) *Pseudogluconobacter saccharoketogenes* 12-15 (FERM BP-1132), *Pseudogluconobacter saccharoketogenes* 12-4 (FERM BP-1131), and *Pseudogluconobacter saccharoketogenes* 22-3 (FERM BP-1133), by mixed culture with bacteria selected from the group consisting of *Bacillus cereus* IFO 3131, *Bacillus licheniformis* IFO 12201, *Bacillus megaterium* IFO 12108, *Bacillus pumilus* IFO 12090, *Bacillus amyloliquefaciens* IFO 3022, *Bacillus subtilis* IFO 13719, *Bacillus circulans* IFO 3967, *Pseudomonas trifolii* IFO 12056, *Pseudomonas maltophilia* IFO 12692, *Proteus inconstans* IFO 12930, *Citorobacter freundii* IFO 13544, *Enterobacter cloacae* IFO 3320, *Erwinia herbicola* IFO 12686, *Xanthomonas pisi* IFO 13556, *Xanthomonas citri* IFO 3835, *Flavobacterium menigosepticum* IFO 12535, *Micrococcus varians* IFO 3765 or *Escherichia coli* IFO 3366, the improvement which comprises separating continuously, by electrodialysis, from the fermentation broth or microbial cell reaction mixture, the produced 2KGA in a free form or as a salt thereof with a univalent or bivalent low molecular-weight cation selected from the group consisting of $Li^+$, $Na^+$, $K^+$, $Ca^{2+}$, $Mg^{2+}$ and $NH_4^+$ as the counter ion of the 2-keto-L-gulonate anion.

2. A process according to claim 1, wherein the electrodialysis is carried out while maintaining the concentration of 2KGA in the fermentation broth or microbial cell reaction mixture at not more than 80 mg/ml.

* * * * *